(12) United States Patent
Nunez et al.

(10) Patent No.: US 8,894,582 B2
(45) Date of Patent: Nov. 25, 2014

(54) CARDIAC PRESSURE MONITORING DEVICE

(75) Inventors: Anthony I. Nunez, Beachwood, OH (US); Harry D. Rowland, East Peoria, IL (US)

(73) Assignee: Endotronix, Inc., Peoria, IL (US)

( * ) Notice: Subject to any disclaimer, the term of this patent is extended or adjusted under 35 U.S.C. 154(b) by 1570 days.

(21) Appl. No.: 12/011,524

(22) Filed: Jan. 25, 2008

(65) Prior Publication Data

US 2009/0054793 A1   Feb. 26, 2009

Related U.S. Application Data

(60) Provisional application No. 60/897,776, filed on Jan. 26, 2007, provisional application No. 60/947,925, filed on Jul. 3, 2007.

(51) Int. Cl.
| | |
|---|---|
| *A61B 5/02* | (2006.01) |
| *A61B 5/0215* | (2006.01) |
| *A61B 5/00* | (2006.01) |
| *A61N 1/05* | (2006.01) |
| *A61N 1/365* | (2006.01) |

(52) U.S. Cl.
CPC .............. *A61B 5/0215* (2013.01); *A61B 5/7203* (2013.01); *A61N 1/36564* (2013.01); *A61N 1/057* (2013.01); *A61N 1/36578* (2013.01); *A61B 5/412* (2013.01); *A61B 2562/0219* (2013.01)
USPC ............................. 600/486; 607/23; 607/126

(58) Field of Classification Search
USPC ............ 600/485–488; 607/12, 119, 122, 126, 607/23
See application file for complete search history.

(56) References Cited

U.S. PATENT DOCUMENTS

| | | |
|---|---|---|
| 3,888,708 A | 6/1975 | Wise et al. |
| 4,023,562 A | 5/1977 | Hynecek et al. |
| 4,407,296 A | 10/1983 | Anderson |
| 4,485,813 A | 12/1984 | Anderson et al. |
| 4,815,472 A | 3/1989 | Wise et al. |
| 4,881,410 A | 11/1989 | Wise et al. |
| 4,953,387 A | 9/1990 | Johnson et al. |
| 5,013,396 A | 5/1991 | Wise et al. |
| 5,046,497 A | 9/1991 | Millar |
| 5,055,838 A | 10/1991 | Wise et al. |
| 5,059,543 A | 10/1991 | Wise et al. |
| 5,108,420 A | 4/1992 | Marks |
| 5,113,868 A | 5/1992 | Wise et al. |
| 5,257,630 A | 11/1993 | Broitman et al. |
| 5,262,127 A | 11/1993 | Wise et al. |
| 5,282,827 A | 2/1994 | Kensey et al. |
| 5,296,255 A | 3/1994 | Gland et al. |

(Continued)

OTHER PUBLICATIONS

An International Search Report for corresponding PCT patent application No. PCT/US08/69229, filed Jul. 3, 2008 (3 pages).

(Continued)

*Primary Examiner* — Navin Natnithithadha
*Assistant Examiner* — Eric Messersmith
(74) *Attorney, Agent, or Firm* — McDonald Hopkins LLC (57) ABSTRACT

A cardiac pressure monitoring device includes a fixation member defining a central opening to facilitate slidably positioning the fixation device about a pacemaker lead wire. At least one sensor is coupled to the fixation member. The at least one sensor is configured to sense a physical, chemical, and/or physiological parameter within a cardiac chamber.

22 Claims, 9 Drawing Sheets

(56) References Cited

U.S. PATENT DOCUMENTS

| | | | |
|---|---|---|---|
| 5,343,064 A | 8/1994 | Spangler et al. | |
| 5,368,040 A | 11/1994 | Carney | |
| 5,377,524 A | 1/1995 | Wise et al. | |
| 5,417,235 A | 5/1995 | Wise et al. | |
| 5,564,434 A * | 10/1996 | Halperin et al. | 600/488 |
| 5,690,674 A | 11/1997 | Diaz | |
| 5,938,602 A * | 8/1999 | Lloyd | 600/424 |
| 5,992,769 A | 11/1999 | Wise et al. | |
| 6,109,113 A | 8/2000 | Chavan et al. | |
| 6,126,675 A | 10/2000 | Shchervinsky et al. | |
| 6,140,144 A | 10/2000 | Najafi et al. | |
| 6,174,322 B1 | 1/2001 | Schneidt | |
| 6,190,400 B1 | 2/2001 | Van De Moer et al. | |
| 6,232,150 B1 | 5/2001 | Lin et al. | |
| 6,309,350 B1 | 10/2001 | VanTassel et al. | |
| 6,331,163 B1 | 12/2001 | Kaplan | |
| 6,338,284 B1 | 1/2002 | Najafi et al. | |
| 6,366,804 B1 | 4/2002 | Mejia | |
| 6,438,408 B1 | 8/2002 | Mulligan et al. | |
| 6,454,720 B1 | 9/2002 | Clerc et al. | |
| 6,471,656 B1 | 10/2002 | Shalman et al. | |
| 6,477,901 B1 | 11/2002 | Tadigadapa et al. | |
| 6,499,354 B1 | 12/2002 | Najafi et al. | |
| 6,592,608 B2 | 7/2003 | Fisher et al. | |
| 6,636,769 B2 | 10/2003 | Govari et al. | |
| 6,645,143 B2 | 11/2003 | VanTassel et al. | |
| 6,647,778 B2 | 11/2003 | Sparks | |
| 6,666,826 B2 | 12/2003 | Salo et al. | |
| 6,667,725 B1 | 12/2003 | Simons et al. | |
| 6,682,490 B2 | 1/2004 | Roy et al. | |
| 6,713,828 B1 | 3/2004 | Chavan et al. | |
| 6,749,622 B2 | 6/2004 | McGuckin, Jr. et al. | |
| 6,764,446 B2 | 7/2004 | Wolinsky et al. | |
| 6,779,406 B1 | 8/2004 | Kuznia et al. | |
| 6,783,499 B2 | 8/2004 | Schwartz | |
| 6,817,983 B1 * | 11/2004 | Millar | 600/488 |
| 6,824,521 B2 | 11/2004 | Rich et al. | |
| 6,838,640 B2 | 1/2005 | Wise et al. | |
| 6,844,213 B2 | 1/2005 | Sparks | |
| 6,855,115 B2 | 2/2005 | Fonseca et al. | |
| 6,890,300 B2 | 5/2005 | Lloyd et al. | |
| 6,893,885 B2 | 5/2005 | Lemmerhirt et al. | |
| 6,916,310 B2 | 7/2005 | Sommerich | |
| 6,923,625 B2 | 8/2005 | Sparks | |
| 6,926,670 B2 | 8/2005 | Rich et al. | |
| 6,932,114 B2 | 8/2005 | Sparks | |
| 6,935,010 B2 | 8/2005 | Tadigadapa et al. | |
| 6,939,299 B1 | 9/2005 | Petersen et al. | |
| 6,959,608 B2 | 11/2005 | Bly et al. | |
| 6,968,743 B2 | 11/2005 | Rich et al. | |
| 6,970,742 B2 | 11/2005 | Mann et al. | |
| 6,981,958 B1 | 1/2006 | Gharib et al. | |
| 7,001,398 B2 | 2/2006 | Carley et al. | |
| 7,004,015 B2 | 2/2006 | Chang-Chien et al. | |
| 7,013,734 B2 | 3/2006 | Zdeblick et al. | |
| 7,028,550 B2 | 4/2006 | Zdeblick et al. | |
| 7,059,176 B2 | 6/2006 | Sparks | |
| 7,066,031 B2 | 6/2006 | Zdeblick et al. | |
| 7,073,387 B2 | 7/2006 | Zdeblick et al. | |
| 7,081,125 B2 | 7/2006 | Edwards et al. | |
| 7,137,953 B2 | 11/2006 | Eigler et al. | |
| 7,147,604 B1 | 12/2006 | Allen et al. | |
| 7,149,587 B2 | 12/2006 | Wardle et al. | |
| 7,162,926 B1 | 1/2007 | Guziak et al. | |
| 7,192,001 B2 | 3/2007 | Wise et al. | |
| 7,198,603 B2 | 4/2007 | Penner et al. | |
| 7,211,048 B1 | 5/2007 | Najafi et | |
| 7,228,735 B2 | 6/2007 | Sparks et al. | |
| 7,274,965 B1 * | 9/2007 | Karicherla et al. | 607/119 |
| 7,645,233 B2 * | 1/2010 | Tulkki et al. | 600/300 |
| 7,899,550 B1 * | 3/2011 | Doan et al. | 607/122 |
| 2002/0045921 A1 | 4/2002 | Wolinsky et al. | |
| 2002/0072656 A1 | 6/2002 | Vantassel et al. | |
| 2002/0115920 A1 | 8/2002 | Rich et al. | |
| 2002/0138009 A1 | 9/2002 | Brockway et al. | |
| 2002/0151816 A1 | 10/2002 | Rich et al. | |
| 2002/0188207 A1 | 12/2002 | Richter | |
| 2003/0136417 A1 | 7/2003 | Fonseca et al. | |
| 2003/0139677 A1 | 7/2003 | Fonseca et al. | |
| 2003/0139771 A1 | 7/2003 | Fisher et al. | |
| 2003/0158584 A1 | 8/2003 | Cates et al. | |
| 2003/0191496 A1 | 10/2003 | Edwards et al. | |
| 2004/0024440 A1 * | 2/2004 | Cole | 607/122 |
| 2004/0102806 A1 | 5/2004 | Broome et al. | |
| 2004/0158138 A1 | 8/2004 | Kilcoyne et al. | |
| 2004/0176672 A1 * | 9/2004 | Silver et al. | 600/345 |
| 2004/0255643 A1 | 12/2004 | Wise et al. | |
| 2004/0260164 A1 | 12/2004 | Kilcoyne et al. | |
| 2005/0013685 A1 | 1/2005 | Ricketts et al. | |
| 2005/0015014 A1 | 1/2005 | Fonseca et al. | |
| 2005/0043601 A1 | 2/2005 | Kilcoyne et al. | |
| 2005/0049634 A1 | 3/2005 | Chopra | |
| 2005/0080346 A1 | 4/2005 | Gianchandani et al. | |
| 2005/0103114 A1 | 5/2005 | Bly et al. | |
| 2005/0154321 A1 | 7/2005 | Wolinsky et al. | |
| 2005/0160825 A1 | 7/2005 | Zdeblick et al. | |
| 2005/0160827 A1 | 7/2005 | Zdeblick et al. | |
| 2005/0187482 A1 | 8/2005 | O'Brien et al. | |
| 2005/0228308 A1 | 10/2005 | Iddan et al. | |
| 2005/0288596 A1 | 12/2005 | Eigler et al. | |
| 2005/0288604 A1 | 12/2005 | Eigler et al. | |
| 2005/0288722 A1 | 12/2005 | Eigler et al. | |
| 2006/0041281 A1 | 2/2006 | Von Arx et al. | |
| 2006/0047205 A1 | 3/2006 | Ludomirsky et al. | |
| 2006/0052821 A1 | 3/2006 | Abbott et al. | |
| 2006/0064133 A1 | 3/2006 | Von Arx et al. | |
| 2006/0064134 A1 | 3/2006 | Mazar et al. | |
| 2006/0064142 A1 | 3/2006 | Chavan et al. | |
| 2006/0064143 A1 | 3/2006 | Von Arx et al. | |
| 2006/0116590 A1 | 6/2006 | Fayram et al. | |
| 2006/0122522 A1 | 6/2006 | Chavan et al. | |
| 2006/0129050 A1 | 6/2006 | Martinson et al. | |
| 2006/0178583 A1 | 8/2006 | Montegrande et al. | |
| 2006/0178695 A1 | 8/2006 | Decant, Jr. et al. | |
| 2006/0206146 A1 | 9/2006 | Tenerz | |
| 2006/0212047 A1 | 9/2006 | Abbott et al. | |
| 2006/0217762 A1 | 9/2006 | Maahs et al. | |
| 2006/0217763 A1 | 9/2006 | Abbott et al. | |
| 2006/0217764 A1 | 9/2006 | Abbott et al. | |
| 2006/0229488 A1 | 10/2006 | Ayre et al. | |
| 2006/0271078 A1 | 11/2006 | Modesitt | |
| 2007/0007240 A1 | 1/2007 | Wise et al. | |
| 2007/0016084 A1 | 1/2007 | Denault | |
| 2007/0028698 A1 | 2/2007 | Guziak et al. | |
| 2007/0032734 A1 | 2/2007 | Najafi et al. | |
| 2007/0049980 A1 | 3/2007 | Zielinski et al. | |
| 2007/0049984 A1 * | 3/2007 | Osypka | 607/32 |
| 2007/0060959 A1 | 3/2007 | Salo et al. | |
| 2007/0073351 A1 | 3/2007 | Zielinski et al. | |
| 2007/0088221 A1 | 4/2007 | Stahmann | |
| 2007/0088388 A1 | 4/2007 | Opolski et al. | |
| 2007/0100215 A1 | 5/2007 | Powers et al. | |
| 2007/0106246 A1 | 5/2007 | Modesitt | |
| 2007/0106328 A1 | 5/2007 | Wardle et al. | |
| 2007/0106333 A1 | 5/2007 | Fernandez | |
| 2007/0112358 A1 | 5/2007 | Abbott et al. | |
| 2007/0118039 A1 | 5/2007 | Bodecker et al. | |
| 2007/0149880 A1 | 6/2007 | Willis | |
| 2007/0160748 A1 | 7/2007 | Schugt et al. | |

OTHER PUBLICATIONS

Abrams, Synopsis of Cardiac Physical Diagnosis, 1989, Lea & Febiger, pp. 25-29.

Ganong, Review of Medical Physiology, 2003, 21st edition, The McGraw-Hill, Inc., Chapter 29, pp. 569-573.

Allen et al., Moss and Adams' Heart Disease in Infants, Children, and Adolescents, including the Fetus and Young Adult, 2001, Lippincott Williams & Wilkins, 6th edition, vol. 1, pp. 288-292.

* cited by examiner

CARDIAC PRESSURE MONITORING DEVICE

CROSS REFERENCE TO RELATED APPLICATIONS

This application claims the benefit of U.S. Provisional Application No. 60/897,776, filed Jan. 26, 2007, and U.S. Provisional Application No. 60/947,925, filed Jul. 3, 2007, which are hereby incorporated by reference in its entirety.

BACKGROUND OF THE INVENTION

This disclosure relates generally to a cardiac pressure monitoring device for use with cardiac intervention systems including, without limitation, pacemakers and defibrillators and, more particularly, to a cardiac pressure monitoring device having at least one pressure sensor located at a predefined radial distance from a center of a lead wire for the cardiac intervention device.

The medical industry has been performing an increasing number of cardiac intervention system implants on patients, the first such case arising in 1958. Since that first initial pacemaker implant numerous other heart controlling and monitoring devices have been developed. These devices work on the principle of placing leads either in one ventricle or two ventricles of the heart. These leads are implanted into the tissue of the heart muscle and sense electrical pulses of the muscle or transmit electrical pulses to the muscle. Although these devices work well for their intended use, it may be desirable to utilize the devices to obtain diagnostic data including physical, chemical, and/or physiological parameter or variable measurements.

BRIEF DESCRIPTION OF THE INVENTION

In one aspect, a cardiac pressure monitoring device is provided. The cardiac pressure monitoring device includes a fixation member defining a central opening to facilitate slidably positioning the fixation device about a pacemaker lead wire. At least one sensor is coupled to the fixation member. The at least one sensor is configured to sense at least one of a physical, chemical, and physiological parameter within a cardiac chamber.

In another aspect, a cardiac pressure monitoring device is provided. The cardiac pressure monitoring device includes a fixation member including an anchoring member anchoring the fixation member with respect to a cardiac chamber wall. A wireless pressure sensor is coupled to the fixation member and configured to monitor cardiac pressure within the cardiac chamber.

In another aspect, a monitoring device is provided. The monitoring device includes an adjustable fixation member defining a central opening to facilitate slidably positioning the adjustable fixation member about an implantable medical device. At least one sensor is coupled to the adjustable fixation member. The at least one sensor is configured to sense at least one of a physical, chemical, and physiological parameter of a cardiac chamber.

In another aspect, a cardiac intervention system is provided. The cardiac intervention system includes an implantable medical device. A cardiac pressure monitoring device is positioned about the implantable medical device. The cardiac pressure monitoring device includes a fixation member defining a central opening to facilitate slidably positioning the fixation member about the implantable medical device. At least one sensor is coupled to the fixation member. The at least one sensor is configured to sense at least one of a physical, chemical, and physiological parameter of a cardiac chamber.

DETAILED DESCRIPTION OF THE INVENTION

The embodiments described herein provide a cardiac pressure monitoring device for use with cardiac intervention systems including, without limitation, pacemakers and defibrillators. In one embodiment, a cardiac intervention device includes a lead wire and one or more pressure sensors located at a predefined radial distance from a center axis of the lead wire. The pressure sensor may be incorporated into a permanent or removable implantable lead wire or fabricated onto a fixation member that is slidable along the pacemaker lead wire into a permanent or desired position. In one embodiment, the pressure sensor is fabricated using a microelectromechanical systems (MEMS) technique and is configured in wireless data transmission communication with an external receiver to facilitate data transmission of parameter measurements to the external receiver for observation by a practicing physician or a patient.

In order to couple a sensor to a lead wire on a cardiac intervention device, the sensor must be very small. Until recently, pressure sensors of the microscale were not available for common use. The development of microelectromechanical systems (MEMS) has enabled small functional systems to be manufactured on a large scale enabling low cost and high volume output of such products.

One such pressure sensor formed using a MEMS technique has an inductive and capacitive nature. The sensor acts as an inductor (L) and a capacitor (C) connected together in parallel, commonly called an LC tank circuit. The geometry of the sensor allows for the deformation of a capacitive plate with increased pressure. This deformation leads to a deflection of the plate and hence a change in the capacitance value of the system. The LC tank circuit also generates an electronic resonating frequency. This resonating frequency is related to the inductive and capacitance values of the circuit and will change with the deflection of capacitor plates under changing pressure. This emitted resonating frequency signal is received by an external wireless receiver and deciphered into a corrrelative pressure reading.

Such devices may also include wireless data transmission ability. The device requires no battery or internal power.

Rather, the device is powered by an electromagnetic (EM) field that is directed towards the inductor coil. The inductor receives energy from the EM field to charge the capacitor, where the value of the capacitance varies with environmental pressure. When the EM field is removed, the inductance and capacitance form a parallel resonant circuit to radiate energy through the inductor which acts as an antenna. This oscillating circuit will then produce inherent radio frequency (RF) signals, which are proportional to the capacitive values of the sensor. The inductor coil serves both as an inductor creating the oscillating RF signals having a frequency proportional to the capacitance of the sensor at a certain pressure, and as an antenna coil emitting the RF signal generated by the LC tank circuitry.

In one embodiment, the pressure sensor includes an inductor/capacitor circuitry assembled in a parallel configuration, or is a piezoelectric, piezoresistive or capacitive pressure sensor. In the inductor/capacitor circuitry, the resonating frequency of the energized circuit will change with the alternating internal pressure of the heart. The sensor transmits sensed or detected pressure readings wirelessly to an external system receiver or a user, such as a doctor, a nurse or a medical technician, through RF signals without the requirements of an internal powering system. In a particular embodiment, the sensor is energized through electromagnetic fields that are directed to a circuitry of the sensor.

The cardiac pressure monitoring device includes one or more sensors that are integrated with or coupled to the pacemaker lead wire. Alternatively, the cardiac pressure monitoring device includes a separate fixation member having one or more pressure sensors that is coupled about the pacemaker lead wire. In one embodiment, the fixation member includes one or more pressure sensors that are manufactured separately using a suitable microelectromechanical systems (MEMS) technique and subsequently coupled to the fixation member using a suitable fixation method.

With the pressure sensor coupled to or integrated with the pacemaker lead wire, the pressure sensor is configured to provide a working surface that is exposed to an internal environment of the ventricle in which the pacemaker lead wire is placed. This exposure to the internal ventricle environment exposes the pressure sensor components to the internal pressure of the heart and allows the pressure sensor to measure and record a corresponding pressure measurement and transmit the pressure measurement to the user. Further, the pressure sensor is positioned in an electrically isolated position with respect to the lead contact portion.

The cardiac pressure monitoring device is intended to be used as a long-term care monitoring device for patients with chronic heart disease, however the cardiac pressure monitoring device may also be used as a short-term care monitoring device. Through the addition of this "piggy back" pressure monitoring device, the physician is able to obtain additional diagnostic data for the patient at a reduced cost.

Although the following disclosure describes a sensor that is configured to measure and/or monitor an internal fluid pressure within the heart to facilitate obtaining data for cardiac pressure analysis, it should be apparent to those skilled in the art and guided by the teachings herein provided that the sensor as described herein may be configured to measure one or more physical, chemical, and/or physiological parameters or variables to facilitate obtaining data for temperature analysis, blood chemical analysis, blood osmolar analysis, and cellular count analysis, for example. The cardiac pressure monitoring device may include a pressure sensor, an optical sensor, a biochemical sensor, a protein sensor, a motion sensor (e.g., an accelerometer or a gyroscope), a temperature sensor, a chemical sensor (e.g., a pH sensor), and/or a genetic sensor, for example.

Figure 1:
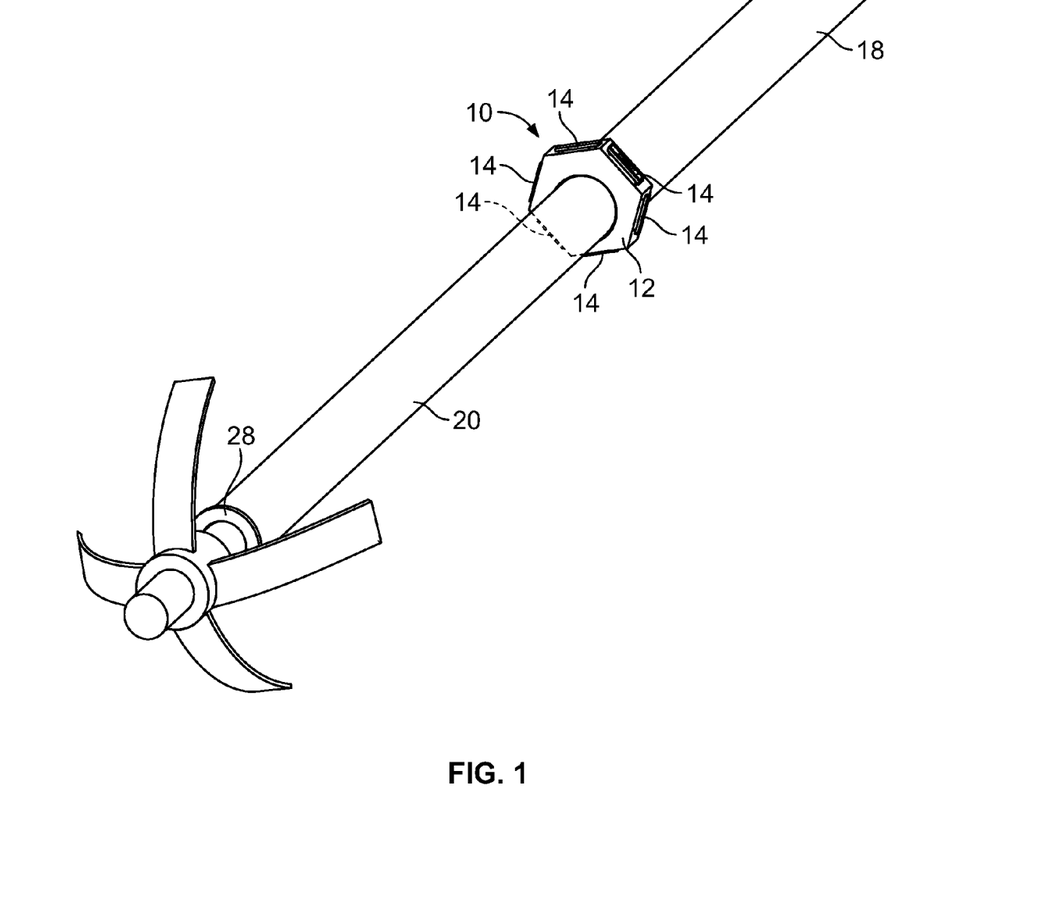
FIG. 1 shows a perspective view of an exemplary cardiac pressure monitoring device including a plurality of pressure sensors coupled to a fixation member mounted over a pacemaker lead wire.
Figure 2:
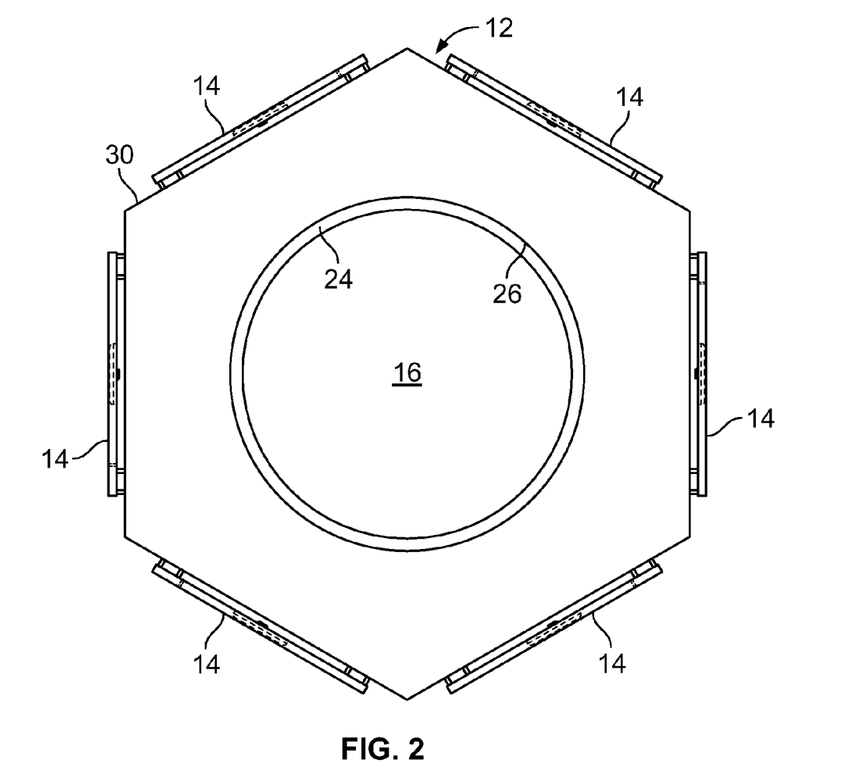
FIG. 2 shows a front view of the cardiac monitoring device shown in FIG. 1.

Referring to FIGS. 1 and 2, in one embodiment, a cardiac pressure monitoring device 10 includes a fixation member 12 and one or more sensors, such as one or more pressure sensors 14, coupled to or integrated with fixation member 12. Fixation member 12 defines a central opening 16, as shown in FIG. 2, to facilitate slidably moving fixation member 12 through an overlapping catheter 18 and positioning fixation member 12 about a pacemaker lead wire 20. In one embodiment, overlapping catheter 18 is subsequently used to urge or push cardiac pressure monitoring device 10 along a length of pacemaker lead wire 20 to properly position and/or secure cardiac pressure monitoring device 10 with respect to pacemaker lead wire 20, as desired, to facilitate obtaining accurate ventricle pressure measurements as required by the physician. Cardiac pressure monitoring device 10 may be positioned as desired before pacemaker lead wire 20 is implanted into the patient's heart or after the initial implantation of pacemaker lead wire 20 into the patient's heart.

Once in place, cardiac pressure monitoring device 10 is configured to remain in the desired or selected position for long-term diagnostic functionality. In one embodiment, placement for long-term functionality is facilitated utilizing a tolerance fitting 24 between a radial inner surface 26 of fixation member 12 defining opening 16 and pacemaker lead wire 20. Alternatively, a spacing tube (not shown) is positioned or inserted between a proximal end of pacemaker lead wire 20 and fixation member 12 to position cardiac pressure monitoring device 10 at a predefined distance from the proximal end of pacemaker lead wire 20.

In an alternative embodiment, cardiac pressure monitoring device 10 is implanted within the patient after pacemaker lead wire 20 has been implanted into the heart. Overlapping catheter 18 overlaps at least a portion of pacemaker lead wire 20 and fits against a surface of fixation member 12 to allow the physician to slide cardiac pressure monitoring device 10 along the length of pacemaker lead wire 20 using overlapping catheter 18. In a particular embodiment, a stop device 28 is positioned about pacemaker lead wire 20 to interfere with fixation member 12 to properly position cardiac pressure monitoring device 10 along the length of pacemaker lead wire 20. Stop device 28 includes a spacer that is placed between a proximal end of pacemaker lead wire 20 and fixation member 12 to ensure that cardiac pressure monitoring device 10 is properly positioned along pacemaker lead wire 20.

In one embodiment, as shown in FIG. 2, fixation member 12 has a general hexagonal cross-sectional area. Alternatively, fixation member 12 may have any suitable cross-sectional area including, without limitation, a circular, triangular, pentagonal, octagonal and other polygonal or non-polygonal cross-sectional area. Referring further to FIG. 2, fixation member 12 defines one or more radially outer surfaces 30. One or more sensors 14 are coupled to or integrated with at least one radially outer surface 30, as described in greater detail below. In an alternative embodiment, one or more sensors 14 are coupled to or integrated with any surface of fixation member 12, such a top surface and/or an opposing bottom surface of fixation member 12. It should be apparent to those skilled in the art and guided by the teachings herein provided that one or more sensors 14 can be coupled to or integrated with any suitable surface of fixation member 12, including radial and non-radial surfaces.

Fixation member 12 is fabricated from a suitable biocompatible material. In one embodiment, fixation member 12 is fabricated from a suitable biocompatible material that facilitates coupling sensor 14 to fixation member 12.

In an exemplary embodiment, one or more sensors 14 are operatively coupled, directly or indirectly, to or incorporated within fixation member 12. Referring further to FIGS. 1 and 2, in one embodiment, one or more sensors 14 are operatively coupled to radially outer surface 30 of fixation member 12 and configured to sense one or more physical, chemical, and/or physiological parameter or variable including, without limitation, a cardiac pressure within the heart. Sensor 14 may be a pressure sensor, an optical sensor, a biochemical sensor, a protein sensor, a motion sensor (e.g., an accelerometer or a gyroscope), a temperature sensor, a chemical sensor (e.g., a pH sensor), or a genetic sensor, for example.

In particular embodiments, sensor 14 includes a capacitive pressure sensing device, a piezoelectric pressure sensing device or a piezoresistive pressure sensing device. In one embodiment, sensor 14 is coupled to radial outer surface 30 of fixation member 12, as shown in FIGS. 1 and 2, and positioned at the cardiac pressure monitoring device/environmental interface. In an alternative embodiment, sensor 14 is integrated with fixation member 12, as shown in FIG. 2, such that sensor 14 is capable of providing high fidelity readings or measurements of cardiac pressure, for example. In a further alternative embodiment, fixation member 12 is a sensor having sensing capabilities.

The dimensions of sensor 14 are dependent on the various parameters in which sensor 14 must operate. In one embodiment, sensor 14 has dimensions smaller than corresponding dimensions of radially outer surface 30 of fixation member 12. In a particular embodiment, sensor 14 has overall dimensions not greater than about 1 millimeter (mm) by about 3 mm, while having a thickness not greater than about 0.5 mm. In one embodiment, the corresponding dimensions of fixation member 12 allow for multiple sensors 14 to be coupled on fixation member 12 while preventing or limiting any disruption in blood flow through the heart. It should be apparent to those skilled in the art and guided by the teachings herein provided, that sensor 14 may have any suitable dimension such that cardiac pressure monitoring device 10 functions as described herein.

Sensor 14 is coupled to fixation member 12 using a suitable biocompatible adhesive including, without limitation, an acrylic-based adhesive, such as cyanoacrylate, an epoxy-based adhesive, a polyurethane-based adhesive, and/or a silicon-based adhesive, such as organopolysiloxane. The use of these adhesives promotes long-term use of cardiac pressure monitoring device 10, while preventing or limiting health risks to the patient. Additionally or alternatively, sensor 14 is coupled to fixation member 12 using a suitable mechanism and/or process known to those skilled in the art and guided by the teachings herein provided including, without limitation, a chemical bonding process, a heat bonding process, a soldering process, a suturing process using a non-absorbable suture, or an outer packaging material. In a particular embodiment, the outer packaging material is chemically treated with a suitable heparin-bonded ePTFE material, a drug eluting material that inhibits cellular overgrowth, such as Tacrolimus or Sirolimus, or another suitable anti-metabolite to provide an anti-thrombotic outer surface. Alternatively, sensor 14 is coated with one or more Heparin-bonded coatings or drug eluting coatings to prohibit or limit clot formation on the exposed sensor surface. In an alternative embodiment, sensor 14 is fabricated or integrated with fixation member 12. In a further alternative embodiment, sensor 14 is fabricated or integrated with pacemaker lead wire 20.

Sensor 14 is coupled to or integrated with fixation member 12 during or after fabrication of fixation member 12. In one embodiment, sensor 14 is coupled to fixation member 12 using a suitable process to minimize restriction and/or obstruction of blood flow through the heart.

In one embodiment, sensor 14 is fabricated using a suitable microelectromechanical systems (MEMS) technology. In a particular embodiment, sensor 14 is fabricated using a MEMS technology that utilizes a resonating frequency of an LC Tank circuit or a suitable capacitive or piezoelectric technology to measure pressure within the heart. Sensor 14 is configured to facilitate transmission of data wirelessly to an external device, such as a user-controlled receiver. In a biomedical application, the signal is desirably transmitted through the patient's surrounding tissue without distorting or lowering a strength of the signal such that the signal is lost or undecipherable. In this embodiment, sensor 14 includes a capacitance inductor circuit arranged in a parallel configuration to form an LC tank circuit. The LC tank circuit generates resonating frequency signals that are transmitted to an at least partially external device, such as a patient signaling device, wherein the signals are processed and deciphered to facilitate treating defects and/or disease, such as cardiovascular disease. Sensor 14 generates a signal representative of a fluid pressure within the heart and the external device generates an output representative of a cardiac pressure within the heart. It should be apparent to those skilled in the art and guided by the teachings herein provided that sensor 14 may be fabricated using any suitable technology and/or process in alternative embodiments.

In one embodiment, sensor 14 is coated with at least one biocompatible material including, without limitation, one or more suitable biocompatible polymers such as a slow release polymer impregnated with an anti-metabolite inhibiting in-tissue growth. In a particular embodiment, at least a portion of sensor 14 is coated with a drug eluding material that prohibits in-tissue growth on sensor 14.

In one embodiment, cardiac pressure monitoring device 10 includes at least one pressure sensor 14 fabricated using MEMS technology. A plurality of pressure sensors 14 may be affixed to or integrated with fixation member 12 to increase accuracy and/or to ensure redundancy. In this embodiment, pressure sensor 14 utilizes a capacitor and inductor circuitry set-up in a parallel configuration. The movement of the two capacitor plates allows for variable capacitance due to changes in pressure. The change in this capacitance changes the resonating frequency of pressure sensor 14 enabling the output signal to be deciphered into a change in pressure. Alternatively, pressure sensor 14 is a capacitive pressure sensing device, a piezoelectric pressure sensing device or a piezoresistive pressure sensing device. In further alternative embodiments, pressure sensor 14 includes any suitable circuitry that facilitates proper operation of pressure sensor 14.

After cardiac pressure monitoring device 10 is implanted for long-term use, pressure sensor 14 is configured to measure an internal ventricle pressure. If an inductor (L) and capacitance (C) circuitry (LC tank) is used, cardiac pressure monitoring device 10 has the ability to transmit the pressure data to a receiver unit wirelessly. In this embodiment, pressure sensor 14 includes circuitry having an inductor and capacitor wired in parallel. The circuitry generates a resonating frequency which is dependant on the inductive and capacitance values of the system. In a particular embodiment, pressure sensor 14 utilizes dual capacitor plates having displacement and capacitance values that change with changing pressure. The change in capacitance values changes the resonating frequency of the RF signals emitted from cardiac pressure monitoring device 10. In medical applications, these emitted RF signals travel through the heart tissues and through the subsequent tissues of the body in order to be interpreted by an external receiver unit.

To lower electrical and magnetic interference and/or noise, which may be seen by the pressure sensor circuitry through the close location to pacemaker lead wire 20, a shielding apparatus may be used to absorb the unwanted noise. One such form of a shielding apparatus may include a very fine conductive mesh which is placed over pacemaker lead wire 20 in the vicinity of pressure sensor 14. This mesh may act as a Faraday cage absorbing the electrical or magnetic noise emitted from pacemaker lead wire 20 or other miscellaneous noise which may be found in the vicinity of pressure sensor 14.

In one embodiment, pacemaker lead wire 20 is encapsulated in an electromagnetic field insulating material to deter the electromagnetic fields generated through the moving current in pacemaker lead wire 20 to interfere with the pressure sensor function. In a further embodiment, pacemaker lead wire 20 is encapsulated with an electrically conductive wire mesh having the ability to absorb unwanted electromagnetic fields and/or RF interference which may otherwise be detected or sensed by pressure sensor 14. The wire mesh or cage may act as a Faraday cage to reduce electrical noise and/or electromagnetic radiation generated by pacemaker lead wire 20 and/or other sources that may interfere with the function of pressure sensor 14 and the pressure sensor RF telemetry function. Other suitable devices and/or methods known to those skilled in the art and guided by the teachings herein provided may be used to insulate pressure sensor 14 from various electrical noise, electromagnetic radiation and/or other signals which may adversely affect the function of pressure sensor 14.

In one embodiment, sensor 14 includes a foot piece configured to couple to pacemaker lead wire 20, such as snap onto or added to pacemaker lead wire 20 using an over-the-wire approach. Sensor 14 can be added to a specific portion of pacemaker lead wire 20 to facilitate electrically isolating sensor 14 from pacemaker lead wire 20. With pacemaker lead wire 20 positioned within the blood stream, sensor 14 may be added by an over-the-wire technique such that sensor 14 is slidably movable along a length of pacemaker lead wire 20. Pacemaker lead wire 20 is then screwed into the cardiac muscle.

Similarly, this clasp approach can be used to add sensor 14 to other implantable devices, such as long term indwelling catheters (Hickman's, Groshong, Vascular Access catheters), Greenfield filters, percutaneous valvular delivery devices, such as mitral valve coronary sinus based delivery catheters. The latter allows for placement of sensor 14 within the right atrium so that changes to the mitral valve can be monitored during the procedure. This is important when conditions of mitral stenosis are created if the percutaneous valve repair leads to an over tightening of the valve. The resultant elevated pulmonary artery pressures lead to elevated right ventricular and right atrial pressures. The placement of wireless sensor 14 on a lead or implantable strut may also allow for measurement of flow, temperature, and/or chemical composition of the blood.

In an alternative embodiment, sensor 14 is introduced over a guidewire placed transvenously or transarterially by percutaneous means, or with an open incision into structures within the human body. The placement of a guidewire into the target organ allows directed placement. The guidewire is used to guide and anchor a wire lead, which would serve as a permanent or semi-permanent implant over which sensor 14 is guided into a structure of the heart. Wireless pressure measurements can then be made.

Figure 3:
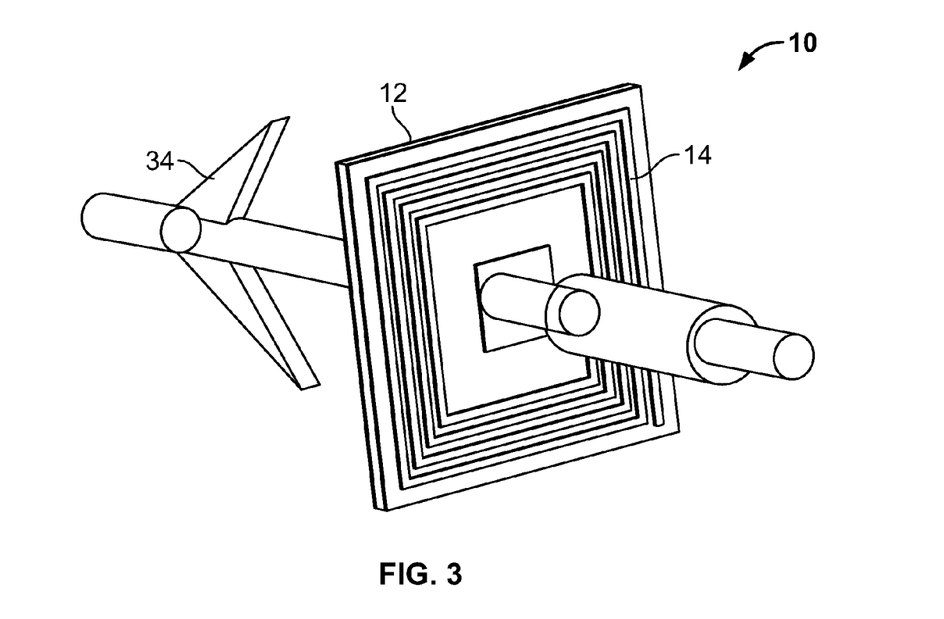
FIG. 3 shows a perspective view of an alternative exemplary cardiac pressure monitoring device.

Referring to FIG. 3, alternatively, a wire is used to deliver cardiac pressure monitoring device 10 including wireless pressure sensor 14 coupled to fixation member 12 to a wall of the cardiac chamber from which a pressure measurement is made. Pressure sensor 14 is guided to the desired portion of the cardiac chamber wall and anchored to the cardiac chamber wall. In one embodiment, an anchoring mechanism, such as a screw or a barb 34, as shown in FIG. 3, anchors pressure sensor 14 to the cardiac chamber wall. The wire is removed leaving an implanted wireless cardiac pressure monitoring device 10 within a desired cardiac chamber.

Figure 4:
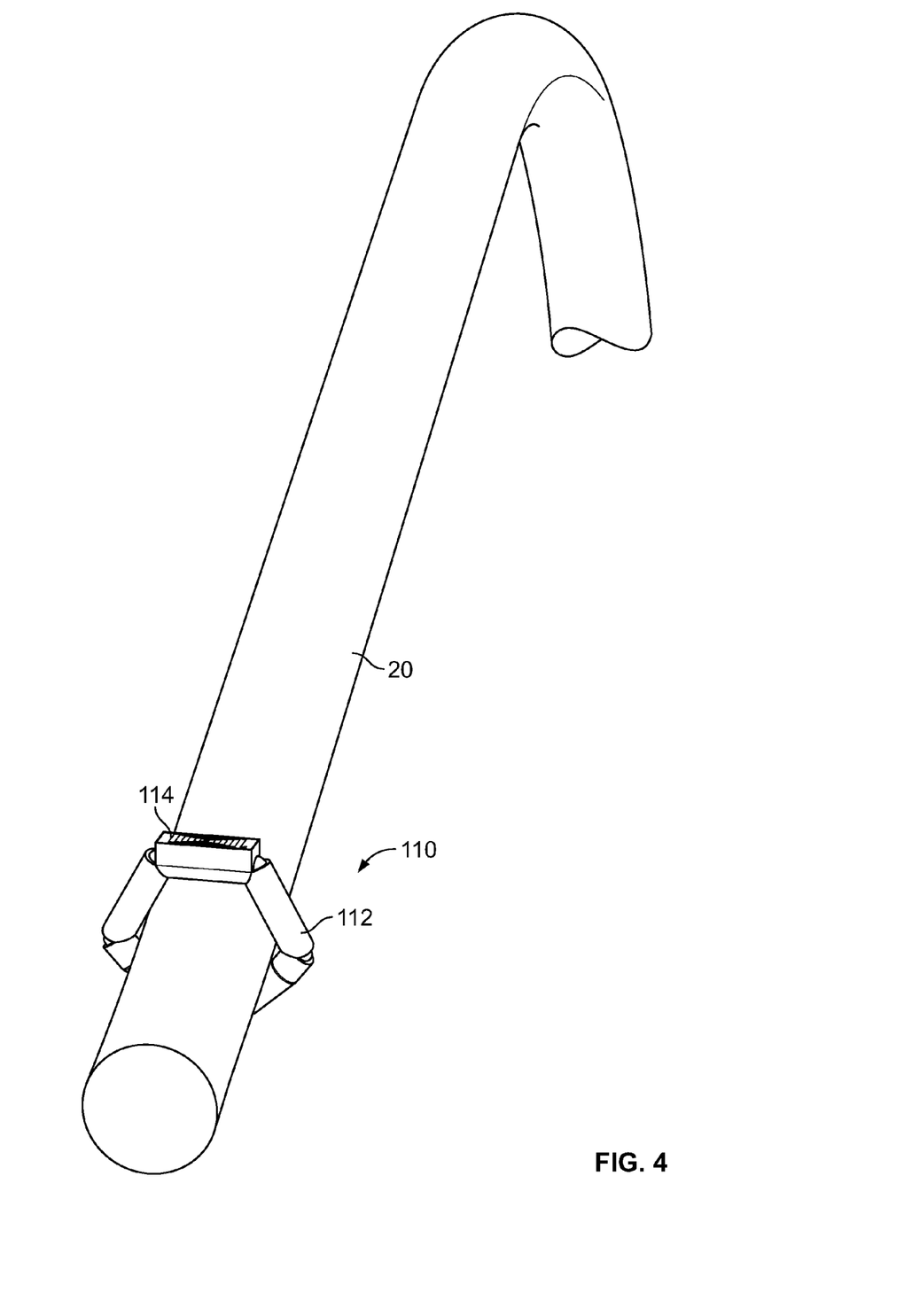
FIG. 4 shows a perspective view of an alternative exemplary cardiac pressure monitoring device including a plurality of pressure sensors coupled to a fixation member mounted over a pacemaker lead wire.
Figure 5:
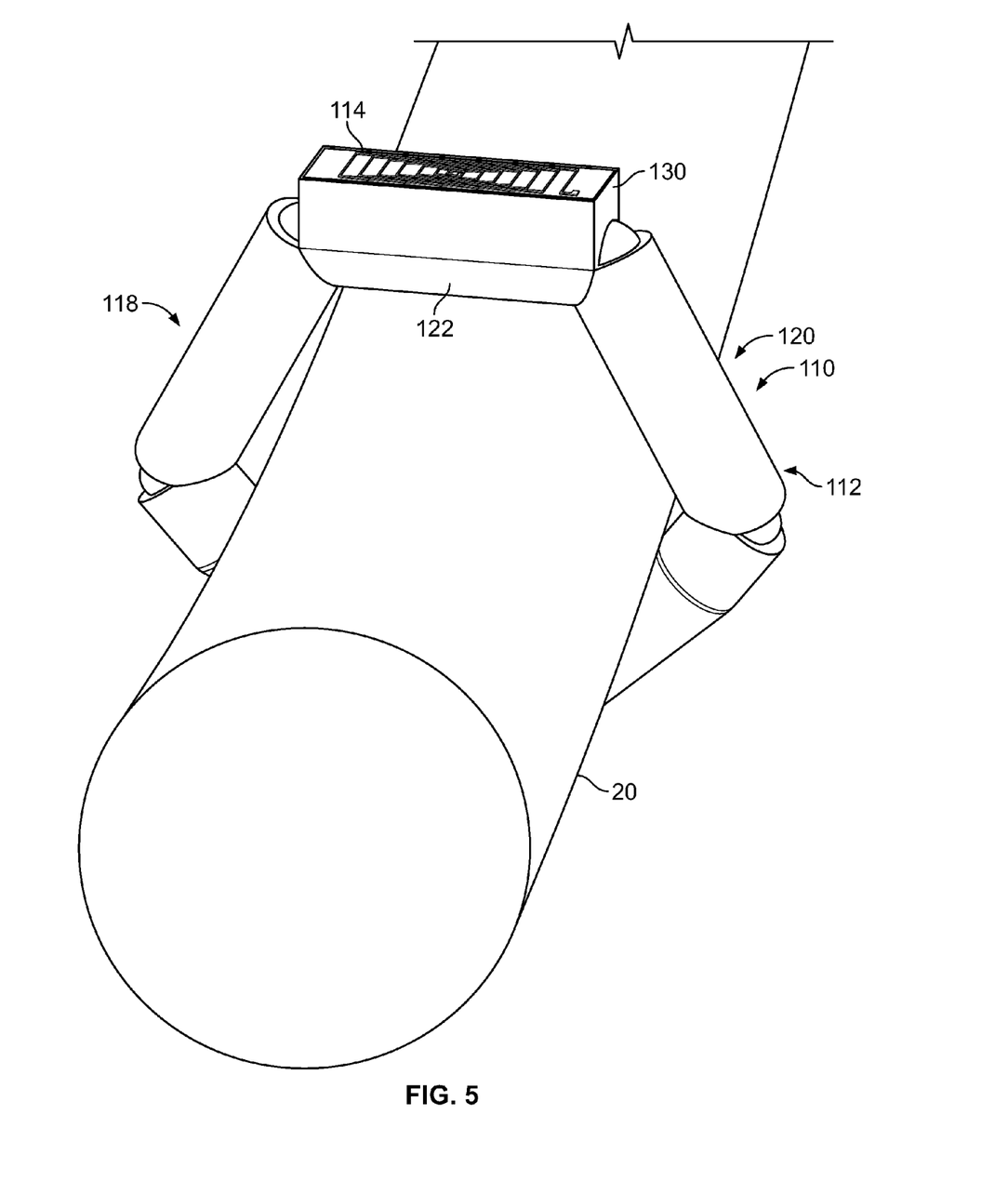
FIG. 5 shows a perspective front view of the cardiac monitoring device shown in FIG. 4.
Figure 6:
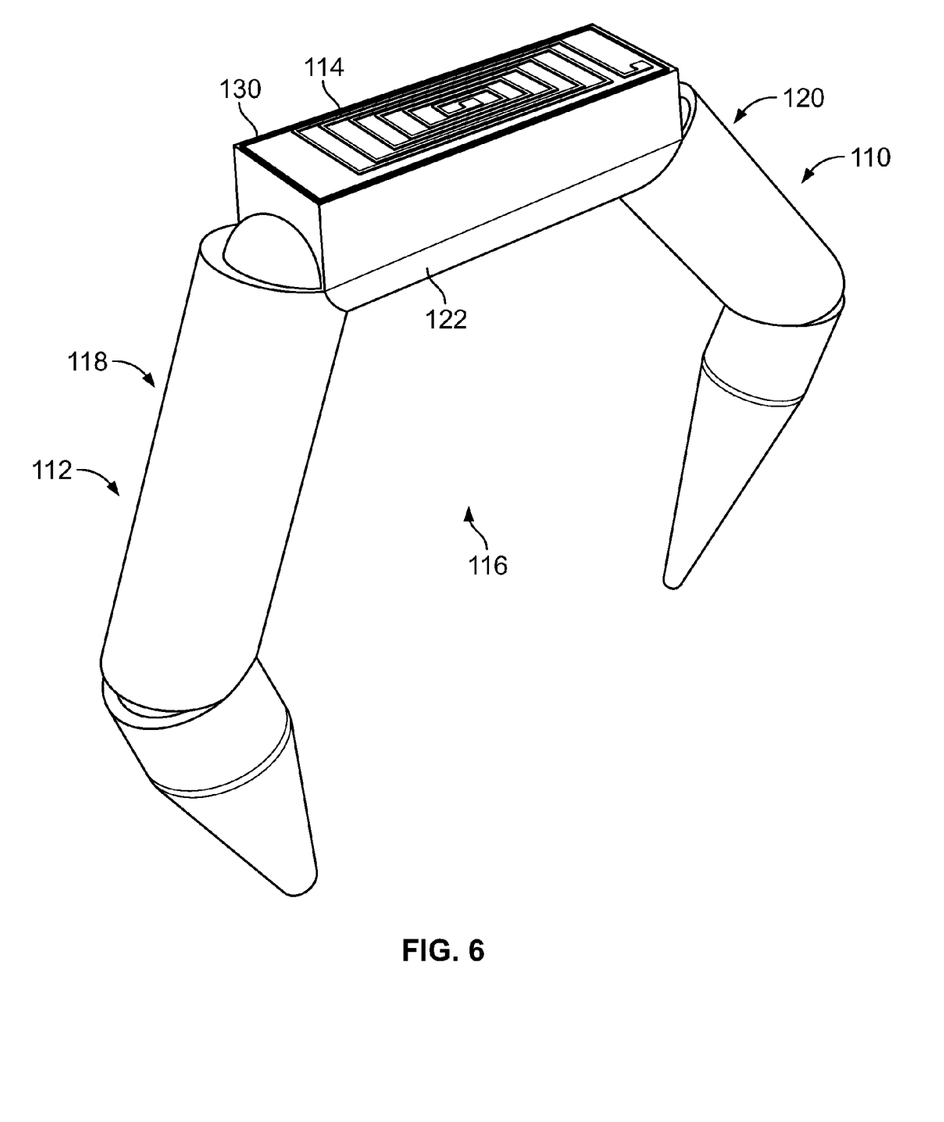
FIG. 6 shows a perspective side view of the cardiac monitoring device shown in FIG. 4.

Referring to FIGS. 4-6, in an alternative embodiment, a cardiac pressure monitoring device 110 includes a fixation member 112 and one or more sensors, such as one or more pressure sensors 114, coupled to or integrated with fixation member 112. Unless otherwise described herein, cardiac pressure monitoring device 110 may include suitable components similar to corresponding components as described above in reference to cardiac pressure monitoring device 10. Fixation member 112 defines a central opening 116, as shown in FIG. 6, to facilitate slidably positioning fixation member 112 about a pacemaker lead wire 20.

As shown in FIGS. 4-6, fixation member 112 includes a plurality of pivotally or rotationally coupled components such that opening 116 defined by fixation member 112 is adjustable to position fixation member 112 about a pacemaker lead wire 20 or another implantable medical device, such as long term indwelling catheters (Hickman's, Groshong, Vascular Access catheters), Greenfield filters, percutaneous valvular delivery devices such as mitral valve coronary sinus based delivery catheters. The latter allows for placement of the sensor within the right atrium during the deployment into the coronary sinus and anchoring within the right atrium allows for the sensor to be piggybacked onto the permanent annular tightening mechanism. The changes to the mitral valve are monitored during the procedure and afterward indirectly based on the degree of pulmonary hypertension and subsequent tricuspid regurgitation that is created when the annulus is tightened.

This is also important when conditions of mitral stenosis are created if the percutaneous valve repair leads to an over tightening of the valve. The resultant elevated pulmonary artery pressures may lead to elevated right ventricular and right atrial pressures. The placement of the wireless sensor on a lead or implantable strut may also allow for measurement of flow, temperature, chemical composition of the blood.

Referring further to FIGS. 5 and 6, fixation member 112 includes a first portion 118 and a generally opposing second portion 120 pivotally or rotationally coupled to a midsection 120. One or more segments are movably coupled together to form first portion 118. Similarly, one or more segments are movably coupled together to form second portion 120. In one embodiment, as shown in FIGS. 5 and 6, a plurality of segments are pivotally and/or rotationally coupled together to form first portion 118. Similarly, a plurality of segments are pivotally and/or rotationally coupled together to form second portion 120. Midsection 122 defines a radially outer surface 130. One or more sensors 14 are coupled to radially outer surface 130 of midsection 122, as shown in FIG. 5, or integrated with radially outer surface 130 of midsection 122, such as described in greater detail above. Sensor 14 is configured to sense one or more physical, chemical, and/or physiological parameter or variable including, without limitation, a cardiac pressure within the heart. Sensor 14 may be a pressure sensor, an optical sensor, a biochemical sensor, a protein sensor, a motion sensor (e.g., an accelerometer or a gyroscope), a temperature sensor, a chemical sensor (e.g., a pH sensor), or a genetic sensor, for example.

Figure 7:
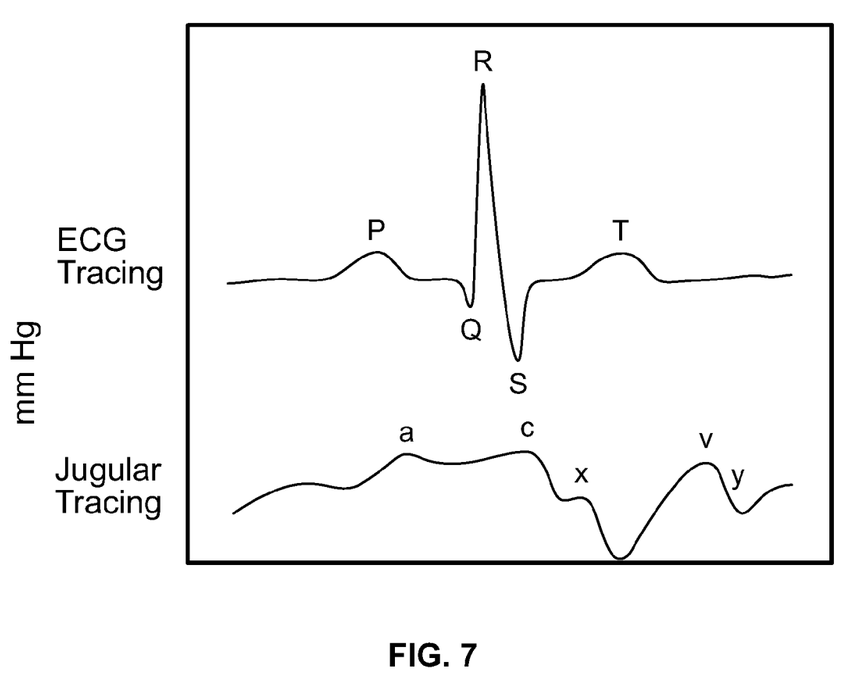
FIG. 7 shows a Right Atrial Pressure (RAP) waveform signal.

Referring to FIGS. 7 and 8A-8C, in one embodiment a Right Atrial Pressure (RAP) and a Left Atrial Pressure (LAP) are monitored using an algorithm developed to reflect changes in the ventricular function of a failing heart. The algorithm may be derived from and at least partially based on a healthy functioning heart. However, pressures within the heart and pressure relationships to the QRS pattern will vary from patient to patient and over time. FIG. 7 illustrates the RAP waveform signal for a healthy functioning heart.

Referring to FIG. 7, normal sinus rhythm can be described as including three positive waves, namely 'a', 'c', and 'v' waves and two negative waves, namely 'x' and 'y' descents. The 'a' wave represents an increased atrial pressure and correlates with the P wave on the corresponding ECG. The 'c' wave represents a slight elevation of the tricuspid valve into the right atrium during early ventricular contraction. The 'v' wave represents the filling of the right atrium against a closed tricuspid valve. The 'x descent' represents the downward movement of the ventricle during systolic contraction. The 'y descent' represents the opening of the tricuspid valve and the flow of blood into the right ventricle.

A LAP signal represents left atrial pressure during normal sinus rhythm and can be described by classical features of the LAP signal. The 'v' wave corresponds to the opening of the mitral valve. The 'a' wave corresponds to atrial contraction. The 'c' wave corresponds to isovolumic contraction and the sequential opening of the aortic valve. The corresponding left atrium volume decreases following the opening of the mitral valve and again at atrial contraction as the left atrium empties its contents into the left ventricle.

The 'z' point (not shown) represents a local minimum value following atrial contraction and closure of the mitral valve immediately preceding ventricular systole. The negative x-wave characteristic or 'x descent' (or systolic collapse) is associated with the descent of the mitral ring during ventricular ejection. The 'y descent' (or diastolic collapse) following the opening of the mitral valve is associated with early ventricular filling and passive atrial emptying.

The diagnosis of various heart conditions requires the monitoring of both peripheral blood pressure and intra-cardiac pressures. Conventional methods for monitoring intra-cardiac pressures are limited to the placement of catheters at the time of cardiac catheterization or the placement of a swan ganz catheter. The swan ganz catheter is placed on the right side of the heart through the central veins to directly monitor the right atrial pressure. The catheter tip is placed in the pulmonary artery and once the catheter tip is positioned within the pulmonary artery, the catheter tip indirectly measures the left ventricular pressure with the mitral valve open during ventricular filling.

The placement of a transseptal device that is able to directly monitor the RAP and the LAP simultaneously allows for the best surrogates for the right ventricular end diastolic pressure (RVEDP) and the left ventricular end diastolic pressure (LVEDP) to be detected or sensed for monitoring the failing heart.

By placing a device with respect to the pulmonary artery to monitor the pulmonary artery pressure, measurements of the pulmonary artery systolic pressure, PA (sys), and the pulmonary artery diastolic pressure, PA (dia), are obtained. PA (sys) is a composite of the right ventricular systolic pressure and the resistance seen across the pulmonary vascular bed. PA (dia) is seen as a surrogate for left ventricular end diastolic pressure when the mitral valve is open, as represented by the 'v' wave in FIG. 7.

Figure 8A:
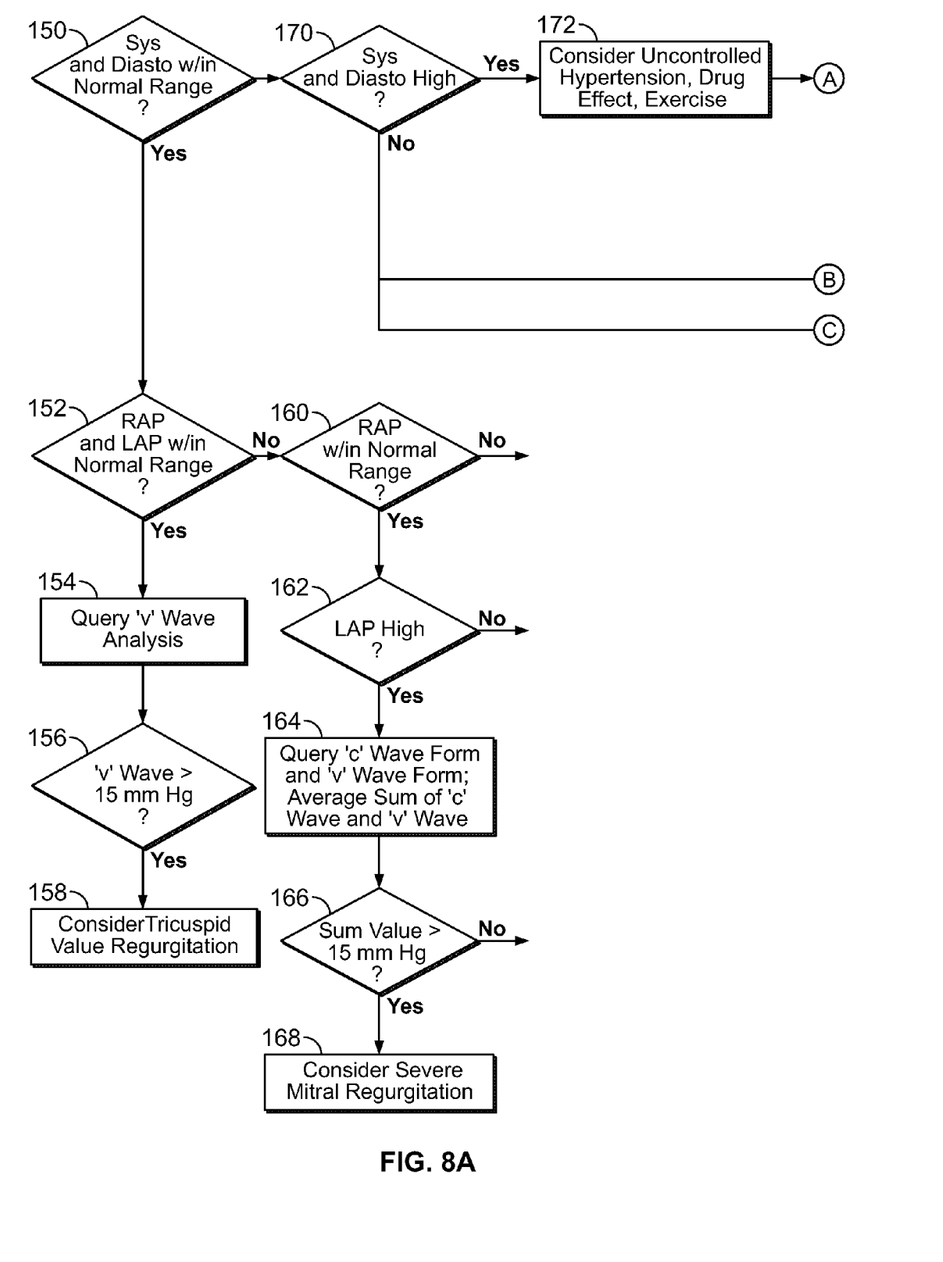
FIGS. 8A-8C show a flow chart describing steps of an algorithm to facilitate a diagnosis of a heart condition.
Figure 8B:
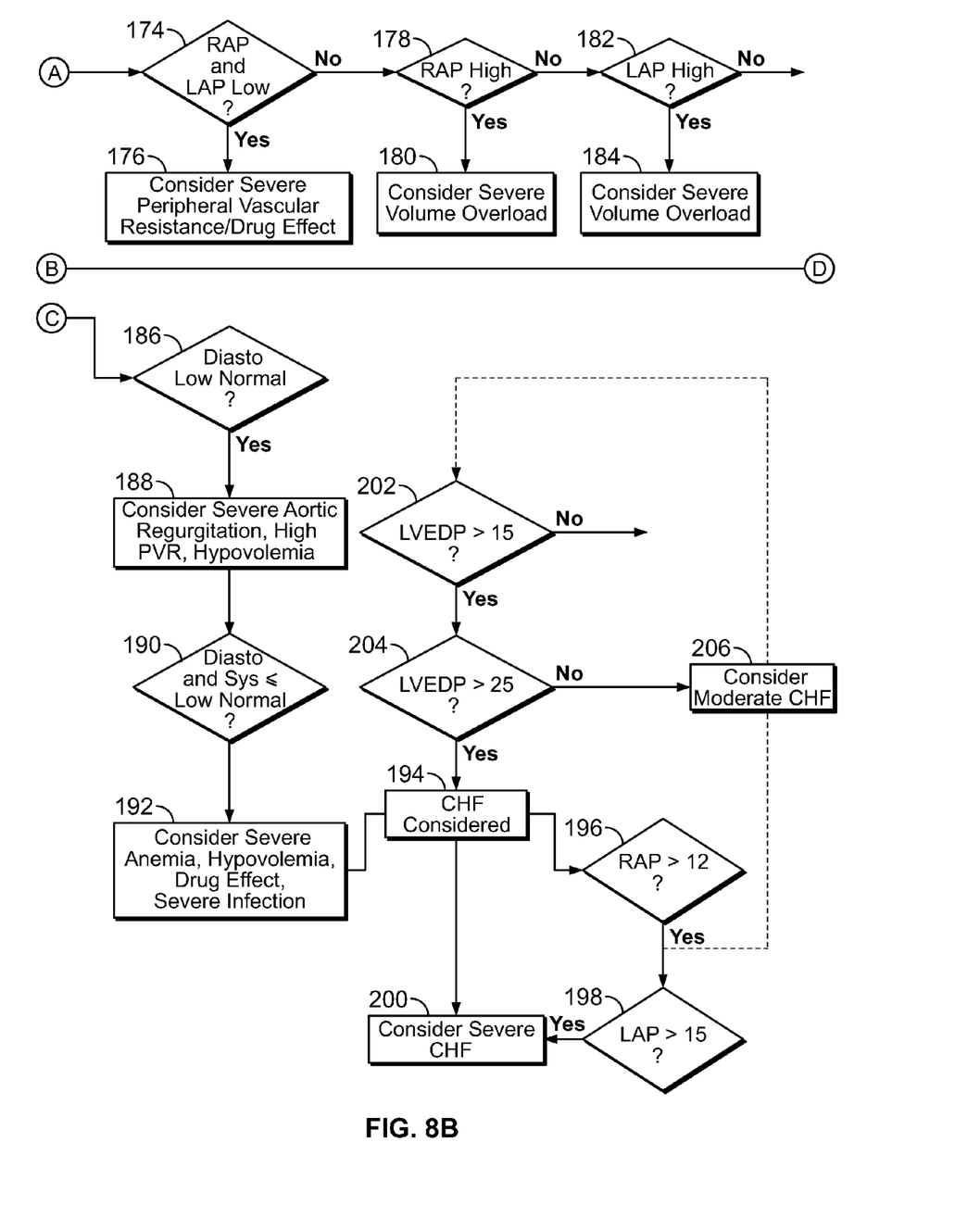
Figure 8C:
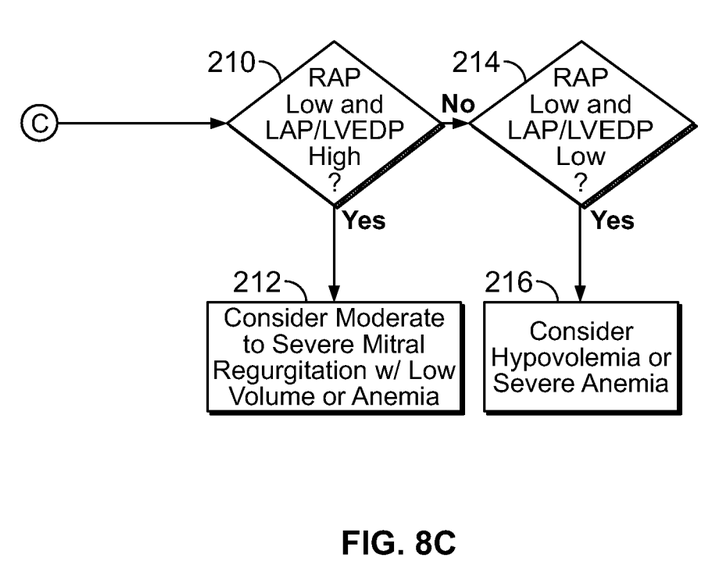

Referring to FIGS. 8A-8C, in one embodiment an algorithm facilitates diagnosis of a heart condition. The following definitions and constraints are utilized in the described algorithm.

Definitions and Constraints:
Males:
Systolic blood pressure (sys) normal range 90<sys<140 mmHg
Diastolic blood pressure (dia) normal range 50>dia<90 mmHg
Females:
Systolic blood pressure (sys) normal range 70>sys<140 mmHg
Diastolic blood pressure (dia) normal range 40>dia<90 mmHg
RAP range 0 mmHg to 12 mmHg
LAP range 0 mmHg to 12 mmHg
RAP high value greater than 12 mmHg
LAP high value greater than 12 mmHg
RAP:
'a' wave values 2-4 mmHg
'c' wave values 4-6 mmHg
'v' wave values 6-10 mmHg
LAP:
'a' wave values 2-4 mmHg
'c' wave values 4-6 mmHg
'v' wave values 6-10 mmHg
LVEDP:
normal range 0-12 mmHg
Moderately High >12 mmHg
Severe >15 mmHg A controller (not shown) includes a processor, a memory, a plurality of input channels, and a plurality of output channels and a computer. As used herein, the term computer is not limited to just those integrated circuits referred to in the art as a computer, but broadly refers to a processor, a microcontroller, a microcomputer, a programmable logic controller, an application specific integrated circuit, and other programmable circuits, and these terms are used interchangeably herein. In the exemplary embodiment, memory may include, without limitation, a computer-readable medium, such as a random access memory. Alternatively, a floppy disk, a compact disc, read only memory (CD-ROM), a magneto-optical disk (MOD), and/or a digital versatile disc (DVD) may also be used. Also, in the exemplary embodiment, a plurality of input channels may represent, without limitation, computer peripherals associated with an operator interface such as a mouse and a keyboard. Alternatively, other computer peripherals may also be used, for example, a scanner. Further, in the exemplary embodiment, a plurality of output channels may include, without limitation, an operator interface monitor.

The controller receives a plurality of inputs from a plurality of sensors, processes the inputs, generates appropriate outputs based on programmed algorithms and discrete circumstances, and transmits signals to the appropriate system components. In one embodiment, the controller receives data from a user, and is configured to run the following algorithm and display the data.

If the systolic pressure and the diastolic pressure are within the normal range 150, 90<sys<140 mmHg for a male patient, for example, and the RAP and the LAP are within the normal range 152, then query 'v' wave analysis 154. If the 'v' wave is determined to be greater then 15 mmHg 156, tricuspid valve regurgitation is considered 158. If the RAP is within the normal range 160 and the LAP is high 162, query the 'c' wave form and the 'v' wave form and average the sum of the 'c' wave and the 'v' wave 164. If the sum value of the 'c' wave and the 'v' wave is greater than 15 mmHg 166, query severe mitral regurgitation 168.

If the systolic pressure and the diastolic pressure are high 170, i.e., greater than or equal to the high normal, as calculated by averaging every $60^{th}$ systolic peak value and every $60^{th}$ diastolic trough value for 24 hours, then uncontrolled hypertension, drug effect, exercise and the RAP is low and the LAP is low 174, then consider severe peripheral vascular resistance or drug effect 176.

If the RAP is high 178, then consider severe volume overload 180. If the LAP is high 182, then consider severe volume overload 184.

In one embodiment, if the diastolic pressure is low normal 186, then consider severe aortic regurgitation, high peripheral vascular resistance (PVR) and hypovolemia 188.

If systolic pressure and diastolic pressure are low 190, i.e, less than or equal to the low normal, as calculated by the averaging of every $60^{th}$ systolic peak value and every $60^{th}$ diastolic trough value for 24 hours, then consider severe anemia, hypovolemia, drug effect, severe infection, such as sepsis and CHF 192.

If CHF is considered 194, then query for the RAP and the LAP. If the RAP is obtained 196 and the value is above 12, then query the LAP 198. If the LAP is obtained 200 and the value is above 15, then consider severe CHF 200.

Alternatively, if the LVEDP is obtained 202 instead of the LAP and this value is greater than 15, then consider moderate CHF 206. If the LVEDP is obtained 204 instead of the LAP and this value is greater than 25, then consider severe CHF 200.

If the systolic pressure and the diastolic pressure are low and the RAP is low and the LAP or the LVEDP is high 210, then consider moderate to severe mitral regurgitation with low volume or anemia 212. If the systolic pressure and the diastolic pressure are low and the RAP is low and the LAP or the LVEDP is low 214, then consider hypovolemia or severe anemia 216.

In one embodiment, the signals are averaged across a 24 hour cycle, a 7 day cycle and/or a 30 day cycle. The rate of rise of the values constitutes a DP/DT value that reflects a change in the function of the heart. If the DP/DT for the RAP or the LAP is greater than 5 mmHg in a 24 hour cycle, then consider early CHF. If the DP/DT for the RAP or the LAP is greater than 10 mmHg in a 7 day cycle, then consider early CHF. If the DP/DT for the RAP or the LAP is greater than 15 mmHg in a 30 day cycle, then consider early CHF.

Based of the analysis of the timing of the troughs for the 'x' descent and the 'y' descent, upon detection of the waveforms, an analysis is made to determine a rate at which the 'x' descent and the 'y' descent occur and a calculation can be made to infer the atrial rate. Movement of the atrial septum has to be accounted for and the pressure waveform generated by a movement of the sensor across the atrial cavity within the blood. The rhythmic movement of the atrial septum may cause an overall rhythmic fluctuation of the RAP and the LAP waveforms in the context of the individual 'a' wave, 'c' wave, and 'v' wave.

In one embodiment, a respiratory variation is superimposed on the waveforms and calibrated into the analysis of the atrial waveforms. If the atrial fibrillation rhythm is present, the rhythm onset is detected in a change in the timing of the inflexion points 'x1' to 'x2' and 'y1' to 'y2'. Once detected, the measurements of the direct values of atrial pressure are determined by averaging a median point of the wave ascents as the wave ascents are sensed. An average of the sensed wave ascents over one minute intervals sampled every 60 minutes for 4 hours are utilized to calculate an average RAP pressure and an average LAP pressure.

Wireless physiological measurement devices, such as cardiac pressure monitoring device 10, are positioned within the human vascular system, such as implanted within the cardiac system, to provide real-time monitoring with interval anatomic and near physiologic measurement devices such as computer axial tomography (CAT) scan, magnetic resonance imaging (MRI) ultrasound based imaging and fluoroscopic based imaging.

The integration of anatomic and physiologic data creates a unique combination akin to the positronic emission tomography (PET) scan and CAT scan combinations currently known as PET/CT.

In one embodiment, a cardiac pressure monitoring device is provided. The cardiac pressure monitoring device includes a fixation member defining a central opening to facilitate slidably positioning the fixation device about a pacemaker lead wire. At least one sensor is coupled to the fixation member. The at least one sensor is configured to sense at least one of a physical, chemical, and physiological parameter within a cardiac chamber.

In an alternative embodiment, a cardiac pressure monitoring device is provided. The cardiac pressure monitoring device includes a fixation member including an anchoring member anchoring the fixation member with respect to a cardiac chamber wall. A wireless pressure sensor is coupled to the fixation member and configured to monitor cardiac pressure within the cardiac chamber.

In a further alternative embodiment, a monitoring device is provided. The monitoring device includes an adjustable fixation member defining a central opening to facilitate slidably positioning the adjustable fixation member about an implantable medical device. At least one sensor is coupled to the adjustable fixation member. The at least one sensor is configured to sense at least one of a physical, chemical, and physiological parameter of a cardiac chamber.

In one embodiment, a cardiac intervention system is provided. The cardiac intervention system includes an implantable medical device. A cardiac pressure monitoring device is positioned about the implantable medical device. The cardiac pressure monitoring device includes a fixation member defining a central opening to facilitate slidably positioning the fixation member about the implantable medical device. At least one sensor is coupled to the fixation member. The at least one sensor is configured to sense at least one of a physical, chemical, and physiological parameter of a cardiac chamber.

In one embodiment, a method for treating cardiovascular disease includes measuring and/or monitoring a patient's blood pressure. A pressure signal is generated that is indicative of the fluid pressure with the arterial and/or venous system of the human body. The delivery of pharmaceutical therapy is controlled based at least partially on the pressure signal. The pressure signal is transmitted to a patient signaling device located at least partially externally to the patient. The pressure signal is processed within the patient signaling device and instructive treatment signals are provided that are based at least partially on the processor output to guide the patient and physician in determining a change in therapy. In a further embodiment, a method is provided for packaging the cardiac pressure monitoring device in a polymer based material, such as an ePTFE (expanded polytetrafluoroethylene) membrane that is covalently bonded with unfractionated heparin or its derivatives. In an alternative embodiment, the cardiac pressure monitoring device is coated with or packaged within a slow release polymer impregnated with Tacrolimus and/or Sirolimus and/or impregnated with carbon. This packaging increases biocompatibility at the blood/device interface by decreasing the likelihood of thrombus formation and/or tissue build-up.

In one embodiment, a method is provided for calibrating the measured pressure against external atmospheric pressure such that the adjusted pressure signal is based in part upon the signal sensor and the obtained atmospheric pressure.

In one embodiment, calibration of the device is initiated at initial manufacture and then at the time of implantation. The device coil is calibrated to a unique frequency signature of the device just prior to implantation with the reader set at atmospheric pressure based on a sea level height at which the procedure is taking place. Once zeroed and deployed, the sensor can then be recalibrated periodically by comparative measurement with standard blood pressure cuff readings. The recalibration of the device can also be performed by ultrasound interrogation. The piezoelectric signal and frequency shift generated by the deflection membrane as a prescribed set ultrasound frequency change can be used to determine a degree of membrane damping occurring as a result of cellular and non-cellular deposition.

In one embodiment, wherein the device includes a plurality of sensors, calibration includes placement of a reference sensor as one of the sensors. The reference sensor provides the ability to internally have affixed a reference point within the blood stream. The capacitance of the reference sensor will change only as a degree of cellular and non-cellular material deposit over time.

The reference sensor allows for calibration in addition to external calibration and accounts for drift in the signal over time based on a change in the materials as they are infiltrated and changed over time.

The multiple sensors also provide the ability to have more than one type of sensor, and up to six sensors in certain embodiments on the device of the same type, and between two and four sensors in alternative embodiments, which allows for summation of the signal or summation to the pressure points being derived. The summation allows averaging of the signal. The averaging of the signal allows for a more even distribution of the data set and increased confidence in the accuracy of the data.

While the invention has been described in terms of various specific embodiments, those skilled in the art will recognize that the invention can be practiced with modification within the spirit and scope of the claims.

What is claimed is:

1. A cardiac pressure monitoring device comprising:
a fixation member defining a central opening and configured to be positioned along the exterior of an implanted lead, the fixation member comprising:
a midsection defining a surface;
a first portion pivotally coupled to said midsection, said first portion comprising at least one first movable segment; and
an opposing second portion pivotally coupled to said midsection, said second portion comprising at least one second movable segment, wherein each of said first movable segment and said second movable segment movable with respect to said midsection to adjust said opening to position said fixation member about an implantable medical device;
at least one sensor coupled to said fixation member and configured to be positioned about the exterior of said lead wire, said at least one sensor configured to sense at least one of a physical, chemical, or physiological parameter;
wherein said fixation member and sensor are movable along the length of said implanted lead and configured to obtain a sensor reading at any position along the length of said implanted lead;
wherein said fixation member is adapted to be slidably positioned along said lead;
a catheter positionable about said lead;
wherein said catheter is adapted to position said fixation member at a desired location along said lead; and
wherein said catheter is further adapted to disengage from said fixation member.

2. A cardiac pressure monitoring device in accordance with claim 1 wherein said at least one sensor is integrated with said fixation member.

3. A cardiac pressure monitoring device in accordance with claim 1 wherein said fixation member has one of a hexagonal, circular, triangular, pentagonal, octagonal, polygonal and non-polygonal cross-sectional area.

4. A cardiac pressure monitoring device in accordance with claim 1 wherein said fixation member defines a radial outer surface, said at least one sensor coupled to said radial outer surface.

5. A cardiac pressure monitoring device in accordance with claim 1 wherein said at least one sensor is configured to sense a pressure within a heart.

6. A cardiac pressure monitoring device in accordance with claim 1 wherein said at least one sensor comprises one of a pressure sensor, an optical sensor, a biochemical sensor, a protein sensor, a motion sensor, an accelerometer, a gyroscope, a temperature sensor, a chemical sensor, a pH sensor, and a genetic sensor.

7. A cardiac pressure monitoring device in accordance with claim 1 wherein said at least one sensor comprises one of a capacitive pressure sensing device, a piezoelectric pressure sensing device, an optical pressure sensing device, an ultrasonic pressure sensing device, a Surface Acoustic Wave (SAW) pressure sensing device, and a piezoresistive pressure sensing device.

8. A cardiac pressure monitoring device in accordance with claim 1 wherein said at least one sensor is coupled to said outer surface using one of an acrylic-based adhesive, an epoxy-based adhesive, a polyurethane-based adhesive, and a silicon-based adhesive.

9. A cardiac pressure monitoring device in accordance with claim 1 wherein said at least one sensor is coupled to said fixation member using one of a chemical bonding process, a heat bonding process, a soldering process, a suturing process using a non-absorbable suture, and an outer packaging material.

10. A cardiac pressure monitoring device in accordance with claim 1 wherein said at least one sensor is coated with one of a heparin-bonded ePTFE material, a drug eluting material, Tacrolimus, Sirolimus, and an anti-metabolite.

11. A cardiac pressure monitoring device in accordance with claim 1 wherein said at least one sensor is fabricated using a suitable microelectromechanical systems (MEMS) technology.

12. The cardiac pressure monitoring device of claim 1, wherein said sensor is a wireless sensor.

13. The cardiac pressure monitoring device of claim 12 further comprising an exterior reader configured to interface with the sensor.

14. The cardiac pressure monitoring device of claim 13, wherein said exterior reader is configured to communicate wirelessly with said sensor.

15. The cardiac pressure monitoring device of claim 1, wherein the catheter is configured to disengage from said fixation member after delivery of said fixation member to a desired location.

16. The cardiac pressure monitoring device of claim 1, wherein the fixation member is positioned at a desired location free of engagement with an interior vessel or chamber wall.

17. A monitoring device comprising:
an adjustable fixation member defining a central opening, wherein the fixation member is configured to be slidably positioned about the exterior of an implantable medical device, the fixation member comprising:
a midsection defining a surface;
a first portion pivotally coupled to said midsection, said first portion comprising at least one first movable segment; and
an opposing second portion pivotally coupled to said midsection, said second portion comprising at least one second movable segment, wherein each of said first movable segment and said second movable segment movable with respect to said midsection to adjust said opening to position said fixation member about an implantable medical device;
at least one sensor coupled to said adjustable fixation member and configured to be positioned about an exterior of said implantable medical device, said at least one sensor configured to sense at least one of a physical, chemical, or physiological parameter; and
wherein said fixation member and sensor are configured to move along the length of said implantable medical device to obtain a sensor reading at any position along the length of said implantable medical device;
wherein said fixation member is adapted to be slidably positioned along a lead;
a catheter positionable about said lead;
wherein said catheter is adapted to position said fixation member at a desired location along said lead; and
wherein said catheter is further adapted to disengage from said fixation member.

18. A monitoring device in accordance with claim 17 wherein said at least one sensor is integrated with said fixation member.

19. A monitoring device in accordance with claim 17 wherein said at least one sensor comprises one of a pressure sensor, an optical sensor, a biochemical sensor, a protein sensor, a motion sensor, an accelerometer, a gyroscope, a temperature sensor, a chemical sensor, a pH sensor, and a genetic sensor.

20. A monitoring device in accordance with claim 17 wherein said at least one sensor is one of coupled to said surface and integrated with said surface.

21. A cardiac intervention system comprising:
an implantable medical device;
a cardiac pressure monitoring device positioned about said implantable medical device, said cardiac pressure monitoring device comprising:
a fixation member defining a central opening to facilitate slidably positioning said fixation member about the exterior of said implantable medical device; said fixation member further comprising:
a midsection defining a surface;
a first portion pivotally coupled to said midsection, said first portion comprising at least one first movable segment; and
an opposing second portion pivotally coupled to said midsection, said second portion comprising at least one second movable segment, wherein each of said first movable segment and said second movable segment movable with respect to said midsection to adjust said opening to position said fixation member about an implantable medical device;
at least one sensor coupled to said fixation member and positioned about an exterior of said implantable medical device, said at least one sensor configured to sense at least one of a physical, chemical, or physiological parameter of a cardiac chamber; and
wherein said cardiac pressure monitoring device is movable along the length of said implantable medical device to obtain a sensor reading at any position along the length of said implantable medical device;
wherein said fixation member is adapted to be slidably positioned along a lead;
a catheter positionable about said lead;
wherein said catheter is adapted to position said fixation member at a desired location along said lead; and
wherein said catheter is further adapted to disengage from said fixation member.

22. A cardiac pressure monitoring device in accordance with claim 21 further comprising a catheter operatively coupled to said implantable medical device and configured to urge said cardiac pressure monitoring device along a length of said implantable medical device.

* * * * *